(12) United States Patent
Gandhi et al.

(10) Patent No.: US 9,872,840 B2
(45) Date of Patent: Jan. 23, 2018

(54) EFFECT OF GARCINOL IN DELAYING THE PROGRESSION OF DIABETIC NEPHROPATHY

(71) Applicant: Delhi Institute of Pharmaceutical Sciences and Research, New Delhi (IN)

(72) Inventors: Sonia Gandhi, Delhi (IN); B. P. Srinivasan, Faridabad (IN)

(73) Assignee: Delhi Institute of Pharmaceutical Sciences and Research, New Delhi (IN)

( * ) Notice: Subject to any disclaimer, the term of this patent is extended or adjusted under 35 U.S.C. 154(b) by 0 days.

(21) Appl. No.: 15/027,200

(22) PCT Filed: Oct. 3, 2013

(86) PCT No.: PCT/IB2013/059089
§ 371 (c)(1),
(2) Date: Apr. 4, 2016

(87) PCT Pub. No.: WO2015/049553
PCT Pub. Date: Apr. 9, 2015

(65) Prior Publication Data
US 2016/0235690 A1    Aug. 18, 2016

(51) Int. Cl.
*A61K 31/122* (2006.01)
*C07C 49/703* (2006.01)
*C07C 49/623* (2006.01)
*A61K 31/047* (2006.01)
*A61K 36/38* (2006.01)

(52) U.S. Cl.
CPC .......... *A61K 31/122* (2013.01); *A61K 31/047* (2013.01); *A61K 36/38* (2013.01); *C07C 49/623* (2013.01); *C07C 49/703* (2013.01)

(58) Field of Classification Search
CPC .... A61K 31/122; A61K 31/047; A61K 36/38; C07C 49/623; C07C 49/703
See application file for complete search history.

(56) References Cited

U.S. PATENT DOCUMENTS

2012/0148692 A1\* 6/2012 Dubey ................ A61K 36/185
424/773

OTHER PUBLICATIONS

Mogensen et al (N Engl J Med. Jul. 12, 1984;311(2):89-93).\*
Villar et al (Nephrol Ther. Dec. 2010;6(7):585-90).\*

\* cited by examiner

*Primary Examiner* — Sudhakar Katakam
(74) *Attorney, Agent, or Firm* — Knobbe Martens Olson & Bear LLP (57) ABSTRACT

The present invention relates to the use of garcinol as a nephroprotective agent. The present invention also relates to the use of garcinol as a therapeutic agent in renal disorders, in particular diabetic nephropathy, and to medicinal preparations containing garcinol. Further disclosed herein are method of treatment of renal disorders, in particular diabetic nephropathy by administration of garcinol.

12 Claims, 3 Drawing Sheets

EFFECT OF GARCINOL IN DELAYING THE PROGRESSION OF DIABETIC NEPHROPATHY

CROSS REFERENCE TO RELATED APPLICATIONS

This application is a U.S. National Phase Application of PCT International Application Number PCT/IB2013/059089, filed on Oct. 3, 2013, designating the United States of America and published in the English language. The disclosures of the above-referenced applications are hereby expressly incorporated by reference in their entireties.

FIELD OF INVENTION

Garcinol, a polyisoprenylated benzophenone, has been studied as an anti-cancer agent. The present invention also relates to the use of garcinol as a nephroprotective agent. The present invention also relates to the use of garcinol as a therapeutic agent in renal disorders, in particular diabetic nephropathy, and to medicinal preparations containing garcinol. The present invention further relates to the method of treatment of renal disorders, in particular diabetic nephropathy by administration of garcinol.

BACKGROUND

Renal/kidney disorders involve an alteration in the normal physiology and function of the kidney. Renal disorders can result from a wide range of acute and chronic conditions and events, including physical, chemical, or biological injury, trauma, disease such as, for example, hypertension, diabetes, congestive heart failure, lupus, sickle cell anemia, and various inflammatory and autoimmune diseases, HIV-associated nephropathies, etc. Renal/kidney disorders can lead to reduced kidney function, hypertension, and renal failure, seriously compromising quality of life, sometimes requiring dialysis and in certain circumstances, kidney transplantation.

Diabetes characterized by chronic hyperglycemia, is a disease as old as mankind. The number of people globally with diabetes mellitus is projected to rise to 439 million by 2030 (Chen et al., 2011). If incidence rates remain the same, the number of youth with type 2 diabetes in the U.S. is projected to increase by a staggering 49 percent over the next 40 years, while the number with type 1 is expected to climb 23 percent, according to a study by the Centers for Disease Control and Prevention, published in the December issue of the year 2012 of Diabetes Care. However, if incidence increases, the number of youth with type 2 could quadruple and the number with type 1 could triple by 2050. Chronic hyperglycemia leads to secondary complications that are more dangerous than hyperglycemia and hence demands constant medical attention and care.

Diabetic nephropathy is a progressive kidney disease caused by angiopathy of capillaries in the kidney glomeruli. It is characterized by nodular glomerulosclerosis due to longstanding diabetes and is a prime cause for dialysis. The syndrome can be seen in patients with chronic diabetes. The disease is progressive and may cause death two or three years after the initial lesions.

Diabetic nephropathy is the most common cause of chronic kidney failure and end-stage kidney disease. People with both type 1 and type 2 diabetes are at risk. The risk is higher if blood-glucose levels are poorly controlled. However, once nephropathy develops, the greatest rate of progression is seen in patients with poor control of their blood pressure.

With increasing incidence of diabetes mellitus in rural population throughout the world and due to adverse effects of synthetic medicine, there is an urgent need for development of indigenous, inexpensive botanical sources for antidiabetic crude or purified drugs.

*Garcinia indica*, is found in Guttiferae plants native to India and South East Asia. Its extract has been used as a food ingredient, cosmetic constituent, as well as a traditional medicine for the treatment of inflammation and other disorders. Its extract is also considered to be used to treat abdominal ailments. Decoction of the fruit of *Garcinia indica* has also been used in treatment of diabetes. Oral administration of *Garcinia indica* rind extract to streptozotocin-induced type 2 diabetic rats has been shown to be effective in decreasing both fasting and postprandial blood glucose.

Garcinol, a polyisoprenylated benzophenone derivative, is one of the major phyto-constituents obtained from a methanolic or hexane extract of rind from *Garcinia indica*. Garcinol is a potent antioxidant and anticancer agent among its other biological effects. Its structure makes it a very efficient scavenger of oxygen free radicals and an excellent inhibitor of nitric oxide. Also, in vitro studies (Baliga M, Bhat H P, Pai R J, Boloor R, Palatty P L. *The chemistry and medicinal uses of the underutilized Indian fruit tree Garcinia indica Choisy (kokum): A review. Food Res Intl.* 2011; 4: 1790-1799) have shown that garcinol suppressed the protein glycation in the bovine serum albumin/fructose system.

SUMMARY OF THE INVENTION

An object of the present invention is to provide an effective, safe and inexpensive botanical source for use as a nephroprotective agent.

An object of the present invention is to provide an effective, safe and inexpensive botanical source for use in the treatment and/or prevention and/or delaying the progression of a renal disorder in a subject in need thereof.

Another object of the present invention is to provide an effective, safe and inexpensive botanical source for use in the treatment and/or prevention and/or delaying the progression of diabetic nephropathy.

Yet another object of the present invention is to provide an effective, safe and inexpensive botanical source for use as a nephroprotective agent.

Yet another objective of the present invention is to provide safe, effective, method for treating and/or preventing and/or delaying progression of renal disorders.

Yet another objective of the present invention is to provide safe, effective, method for treating and/or preventing and/or delaying progression of diabetic nephropathy.

Yet another object of the present invention is to provide an effective, safe composition comprising an inexpensive and safe botanical source, garcinol for use in preventing and/or treating and/or delaying the progression of a renal disorder.

Yet another object of the present invention is to provide an effective, safe composition comprising an inexpensive and safe botanical source, garcinol for use in preventing and/or treating and/or delaying the progression of nephropathy.

Accordingly, the subject matter described herein directed to garcinol and composition comprising garcinol for use in preventing and/or treating and/or delaying the progression of a renal disorder, in particular diabetes nephropathy, in a subject in need thereof.

The subject matter described herein is also directed to a method for treating and/or preventing and/or delaying progression of renal disorders, in particular diabetes nephropathy, in a subject in need thereof, comprising administering to said subject a therapeutically effective amount of garcinol.

DESCRIPTION

The present invention relates to garcinol and its use in preventing and/or treating and/or delaying the progression of a renal disorder, in particular diabetes nephropathy, in a subject. The efficacy of garcinol in the prevention and/or treatment and/or delaying the progression of renal/kidney disorders has also been compared with a reference antidiabetic drug, glimepiride and a standard drug for diabetic nephropathy, olmesartan medoxomil.

Another aspect of the present invention relates to a method for treating and/or preventing and/or delaying progression of renal disorders in a subject in need thereof, comprising administering to said subject a therapeutically effective amount of garcinol.

Another aspect of the present invention relates to a method for treating and/or preventing and/or delaying progression of diabetic nephropathy in a subject in need thereof, comprising administering to said subject a therapeutically effective amount of garcinol.

In an embodiment, the invention pertains, at least in part, to a method for decreasing the rate of increase of serum creatinine in a subject having nephropathy, e.g. diabetic nephropathy. The method includes administering to the subject a therapeutically effective amount of garcinol, such that the rate of increase of serum creatinine is decreased.

In another embodiment, the invention pertains, at least in part, to a method for maintaining reducing albuminuria in a subject having nephropathy, e.g. diabetic nephropathy. The method includes administering to the subject a therapeutically effective amount of garcinol, such that the albuminuria in said subject is stabilized or reduced.

In another embodiment, the invention pertains, at least in part, to a method of increasing the plasma protein levels in a subject having nephropathy, e.g. diabetic nephropathy. The method includes administering to the subject a therapeutically effective amount of garcinol, such that plasma protein levels are increased.

In another embodiment, the invention pertains, at least in part, to a method of increasing the expression of nephrin in the kidney in a subject having nephropathy, e.g. diabetic nephropathy. The method includes administering to the subject a therapeutically effective amount of garcinol, such that expression of nephrin is increased, leading to improved glomerular filter integrity.

In another embodiment, the invention pertains, at least in part, to a method for decreasing the rate of increase of cystatin c in a subject having nephropathy, e.g. diabetic nephropathy. The method includes administering to the subject a therapeutically effective amount of garcinol, such that the rate of increase of cystatin c is decreased.

In another embodiment, the invention pertains, at least in part, to a method for decreasing the rate of increase of (Beta-2 Microglobulin-B2M) in a subject having nephropathy, e.g. diabetic nephropathy. The method includes administering to the subject a therapeutically effective amount of garcinol, such that the rate of increase of B2M is decreased.

In another embodiment, the invention pertains, at least in part, to a method of increasing the erythopoeitin levels in a subject having nephropathy, e.g. diabetic nephropathy. The method includes administering to the subject a therapeutically effective amount of garcinol, such that erythopoeitin levels are increased.

In another embodiment, the invention pertains, at least in part, to a method of increasing the adiponectin levels in a subject having nephropathy, e.g. diabetic nephropathy. The method includes administering to the subject a therapeutically effective amount of garcinol, such that adiponectin levels are increased.

In another embodiment, the invention pertains, at least in part, to a method of reducing glomerulosclerosis significantly, which leads to reduction of (Transforming Growth Factor-beta) TGF-β1 and (Vascular endothelial growth Factor) VEGF in a subject having nephropathy, e.g. diabetic nephropathy. The method includes administering to the subject a therapeutically effective amount of garcinol, such that glomerulosclerosis is reduced.

In another embodiment, the invention pertains, at least in part, to a method of reducing nitric Oxide, in a subject having nephropathy, e.g. diabetic nephropathy. The method includes administering to the subject a therapeutically effective amount of garcinol, such that the Nitric Oxide is reduced.

In another embodiment, the invention pertains, at least in part, to a method of reducing apoptosis, in a subject having nephropathy, e.g. diabetic nephropathy. The method includes administering to the subject a therapeutically effective amount of garcinol, such that the apoptosis is reduced.

In another embodiment, the invention pertains, at least in part, to a method of attenuating tubulointerstitial fibrosis, in a subject having nephropathy, e.g. diabetic nephropathy. The method includes administering to the subject a therapeutically effective amount of garcinol, such that there is a decrease in expression of desmin expression preserves podocytes which leads to attenuation tubulointerstitial fibrosis.

In yet another embodiment, the invention includes a method for improving renal function or delaying progression of renal disorder in a subject having nephropathy, e.g. diabetic nephropathy. The method includes administering to the subject a therapeutically effective amount of garcinol such that renal function is improved or progression of the renal disorder is delayed.

The invention also pertains, at least in part, to a pharmaceutical composition for treating and/or preventing and/or delaying the progression of renal disorders, e.g. diabetic nephropathy, comprising a therapeutically effective amount of garcinol.

The disorders that may be treated are "renal disorder", means any alteration in normal physiology and function of the kidney. This can result from a wide range of acute and chronic conditions and events, including physical, chemical or biological injury, insult, trauma or disease, such as for example hypertension, diabetes, congestive heart failure, lupus, sickle cell anemia and various inflammatory, infectious and autoimmune diseases, HIV-associated nephropathies etc. This term includes but is not limited to diseases and conditions such as kidney transplant, nephropathy; chronic kidney disease (CKD); Glomerulonephritis; inherited diseases such as polycystic kidney disease; nephromegaly (extreme hypertrophy of one or both kidneys); nephrotic syndrome; end stage renal disease (ESRD); acute and chronic renal failure; interstitial disease; nephritis; sclerosis, an induration or hardening of tissues and/or vessels resulting from causes that include, for example, inflammation due to disease or injury; renal fibrosis and scarring; renal-associated proliferative disorders; and other primary or secondary nephrogenic conditions. Fibrosis associated with dialysis following kidney failure and catheter placement, e.g., peritoneal and vascular access fibrosis, is also included.

In some embodiment, the renal disorder or kidney disease may be generally defined as a "nephropathy. The terms "nephropathy" encompass all clinical-pathological changes in the kidney which may result in kidney fibrosis and/or glomerular diseases (e.g. glomerulosclerosis, glomerulonephritis) and/or chronic renal insufficiency, and can cause end stage renal disease and/or renal failure. Some aspects of the present invention relate to compositions and their uses for the prevention and/or treatment of hypertensive nephropathy, diabetic nephropathy, and other types of nephropathy such as analgesic nephropathy, immune-mediated glomerulopathies (e.g. IgA nephropathy or Berger's disease, lupus nephritis), ischemic nephropathy, HIV-associated nephropathy, membranous nephropathy, glomerulonephritis, glomerulosclerosis, radiocontrast media-induced nephropathy, toxic nephropathy, analgesic-induced nephrotoxicity, cisplatin nephropathy, transplant nephropathy, and other forms of glomerular abnormality or injury; glomerular capillary injury (tubular fibrosis). In some embodiments, the terms "nephropathy" or refers specifically to a disorder or disease where there is either the presence of proteins (i.e. proteinuria) in the urine of a subject and/or the presence of renal insufficiency. In some embodiments, the terms "nephropathy" also encompass clinical-pathological changes in the kidney which may result in vascular complications and inflammation of pancreas.

The subject in need includes living organisms in which renal disorders or nephropathy can occur, or which are susceptible to kidney disorder or nephropathy. The term "subject" includes animals (e.g., mammals, rodents, e.g., mice or rats. Preferably, the subject is a mammal. More preferably, the subject is a human.

In some embodiments, the subject is at risk of, or has been diagnosed with, a kidney disease. In various embodiments, the subject is a human patient having or progressing towards stage I kidney disease, stage II kidney disease, stage III kidney disease, stage IV kidney disease or stage V kidney disease. In some embodiments, the methods, compounds or compositions of the invention are effective in stabilizing or in improving the patient's kidney disease ((e.g. from stage V to stage IV, or from stage IV to stage III, or from stage III to stage II, or from stage II to stage I).

In some embodiments, the subject is at risk of or has been diagnosed with diabetes. In some embodiments, the subject is a human patient with type 2 diabetes. In some embodiments, the subject is a human patient with type 1 diabetes.

In specific preferred embodiments of the present aspect the renal disorder is diabetic nephropathy.

The terms "effective amount" or "therapeutically effective amount" are used interchangeably herein and refer to the amount of a compound which is effective to treat a subject, e.g., treat a subject for nephropathy (e.g., diabetic nephropathy), and/or a related complication or treat a subject having an underlying disease. The therapeutically effective amount may vary based on the particular disorder(s) the subject is suffering from, the age, weight, and lifestyle of a particular subject. In addition, the therapeutically effective amount may depend on the subject's blood parameters (e.g. lipid profile), the severity of the disease state, organ function, kidney function, or underlying disease or complications.

In another specific embodiments the therapeutically effective amount of garcinol that may be administered, be in the range of from 100 mg/kg/day to 1000 mg/kg/day.

In yet another specific preferred embodiments the therapeutically affective amount of garcinol that may be administered, is about 200 mg/kg/day.

In yet another specific preferred embodiment the garcinol is administered orally or by injection.

In specific preferred embodiments, the composition of the present invention further comprises pharmaceutically acceptable excipients.

The term "pharmaceutically acceptable" refers to drugs, medicaments, inert ingredients etc., which the term describes, suitable for use in contact with the tissues of humans and lower animals without undue toxicity, incompatibility, instability, irritation, allergic response, and the like, commensurate with a reasonable benefit/risk ratio.

The garcinol used in the invention is used in a plant extract, or is isolated from a plant extract, or is synthetically prepared. In particular garcinol may be obtained from the fruit rind of the plant *Garcinia indica* or it may be synthetically prepared.

The garcinol used in the invention may be isolated form *G. indica* dried fruit (Kokum) rind with ethanol. The process for extraction comprises the following steps:—Extracting *G. indica* dried fruit (Kokum) rind was with ethanol; fractionating the extract by ODS (octadecyl silica) column chromatography eluted stepwise with 60-80% aqueous ethanol; concentrating the fractions containing garcinol and drying in vacuum; dissolving the residue in hexane; cooling the solution at around 5° C. for around for around 2 days; collecting the yellow amorphous precipitate from the solution and washing with cold hexane and recrystallizing at room temperature; obtaining pale yellow needle crystals of garcinola from the solvent.

EXAMPLE

The Garcinol used for the experimental studies was bought from Sami Labs, Hyderabad. It was administered at the dose of 200 mg/kg dispersed in water with 1% CMC. Further, the experimental procedures were conducted according to the Institutional Animal Ethical Committee (protocol no. DIPSAR/IAEC/2009/01) and CPCSEA guidelines. All rats were housed under conventional conditions with controlled temperature, humidity and light (12 hours light-dark cycle), and were provided with a standard commercial diet and water (ad libitum). Healthy albino rats of Wistar strain were kept for breeding. Diabetes was induced by administration of streptozotocin (STZ, 90 mg/kg, i.p.) to a group of 2 day old pups. Age-matched control rats were given an equal volume of vehicle and considered as 'Normal' group of rats. Six weeks after injection, the blood glucose level was measured from the tail vein. Rats with a fasting blood glucose level over 160 mg/dl were considered as diabetic.

After 6 weeks, four groups of animals, each comprising of 8 animals were made. The groups were assigned to receive vehicle or garcinol (200 mg/kg dispersed in 1% CMC); Olmesartan (6 mg/kg/day) and Glimepiride (1 mg/kg/day) once daily for 8 weeks. After the final drug administration, body weight was measured and blood samples were collected in both fasting and post prandial conditions. The kidney of treated and untreated animals were isolated and fixed in 10% buffered formalin solution to prepare paraffin sections.

Body Weight and Metabolic Parameters in Blood

When compared with diabetic group, no significant change in the body weight was observed in rats treated with garcinol after 8 weeks. The results are provided in Table 1 below:

GLUT-2 Expressions in Liver and GLUT-4 Expressions in Soleus Muscle

Figure 3:
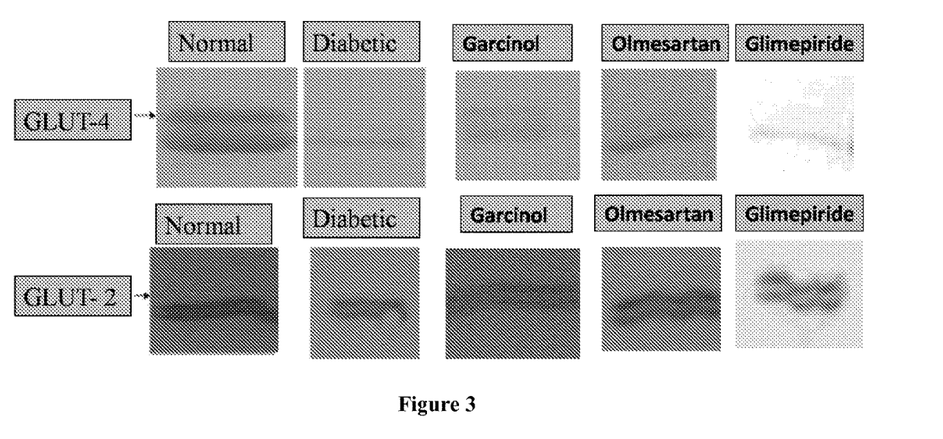
FIG. 3: illustrates the effects of administration of Garcinol on GLUT-4 expression in the muscles (A) and GLUT-2 expression in the liver (B) of diabetic rats along with reference standards of glimepiride and olmesartan

For determination of glucose transporter 2 (GLUT2) protein expressions in liver and glucose transporter 4 (GLUT4) protein expressions in skeletal muscle; each sample prepared was mixed with 1% sodium dodecyl sulfate and 50 mM dithiothreitol, and the mixture was subjected to electrophoresis with 10% polyacrylamide gel. The separated proteins on the gel were electrotransferred to a polyvinylidene difluoride membrane. After blocking with 5% skim milk solution including 0.05% Poly (Oxyethylene) sorbitan monolaurate (Tween 20) overnight at 4° C., the membrane was reacted with anti-GLUT-2 antibody (Abcam, UK) & anti-GLUT-4 antibody (Abcam, UK) for 2 h. Subsequently, it was incubated with horseradish peroxidase conjugated IgG (diluted 1:2000) [Jackson immunoresearch laboratories, USA] for 2 h at room temperature (Western Blot). Reduced qualitative expression of GLUT2 and GLUT 4 in liver and muscle respectively of diabetic rats were improved with the garcinol treatment (FIG. 3), which were better than observed with olmesartan. Glimepiride did not show any improvement in the expressions.

TABLE 1

Effect of Garcinol on body weight and blood glucose

| | Body weight (g) | | | Blood glucose (mg/dl) | | |
| | | | | Fasting | | Post Prandial |
| | Before treatment | After treatment | Before treatment | After treatment | Before treatment | After treatment |
| --- | --- | --- | --- | --- | --- | --- |
| Normal | 141.7 ± 3.8 | 231.7 ± 4.6*** | 84 ± 2.3 | 79 ± 5.67*** | 114 ± 6.01 | 113 ± 5.55*** |
| Diabetic | 131.7 ± 4.4 | 198.3 ± 3.1 | 165 ± 4.83### | 164.2 ± 6.5 | 311 ± 13 | 302 ± 8.25 |
| Garcinol (200 mg/kg) | 141.7 ± 8.3 | 210.2 ± 3.74 | 166.2 ± 4.9### | 136.2 ± 5.86*** | 287 ± 24.7 | 190 ± 5.27*** |
| Olmesartan (6 mg/kg/day) | 145.8 ± 7.6 | 216.7 ± 4.77* | 162.7 ± 4.34*** | 139.7 ± 5.05** | 288 ± 6.82 | 259 ± 7.16** |
| Glimepiride (1 mg/kg/day) | 140.8 ± 5.6 | 208.3 ± 3.1 | 165.2 ± 1.5*** | 119.2 ± 5.4*** | 308 ± 4.98 | 174 ± 3.75*** |

The values are the means ± S.E.M. from eight animals in each group,
p < 0.001 vs. normal group,
*p < 0.05;
**p < 0.01;
***p < 0.001 vs. diabetic group.

Further, groups treated with garcinol showed significant reduction of fasting blood glucose [p<0.001; almost 18%], followed by that of olmesartan, used in diabetic nephropathy [14%]. However, the decrease was less than antidiabetic reference glimepiride treatment (~27%). Moreover, the reduction of post prandial glucose with garcinol treatment (~36%) was more than olmesartan (~10%) but was lower than observed with glimepiride treatment (almost 43%) when compared to diabetic group.

Measurement of α-Glucosidase Inhibitory Activity In Vitro

Figure 1:
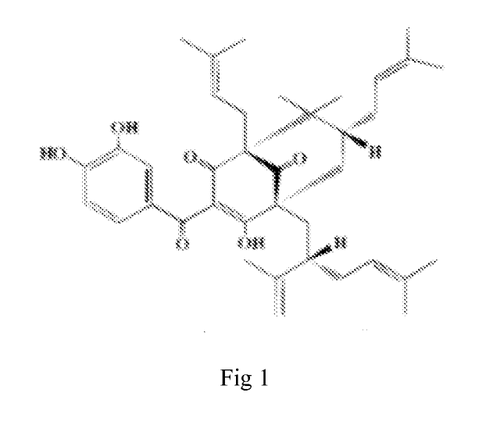
FIG. 1: illustrates the structure of Garcinol
Figure 2:
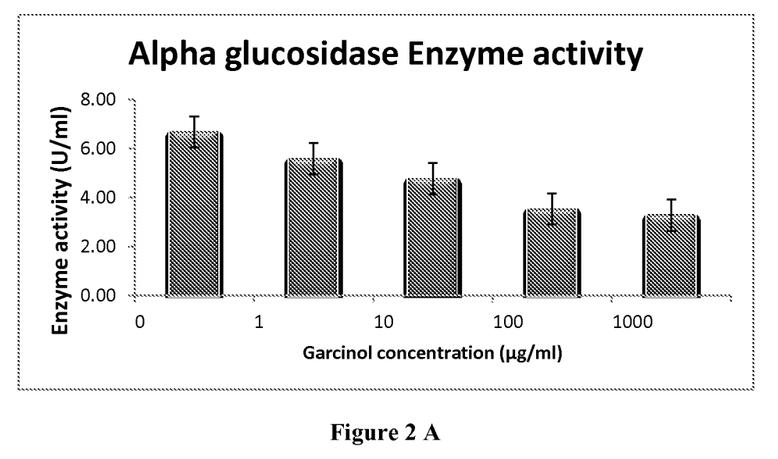
FIG. 2A-B: illustrates the activity and inhibition of enzyme alpha-glucosidase by Garcinol in vitro.

The α-glucosidase inhibitory activity was determined according to Earnst et al., 2005, by measuring the release of 4-nitrophenol from 4-nitrophenyl α-d-glucopyranoside (4-NPGP). The assay procedure was according to the protocol of a micro-well kit. The assay procedure was according to the protocol of a micro-well kit. In vitro studies demonstrated that garcinol possesses dose dependent α-glucosidase inhibitory activity. Almost 50% inhibition of the enzyme was observed with the concentration of 1000 μg/ml of garcinol. The results are presented in FIG. 2A-B.

HOMA-Index and β-Cell Function

Homeostatic Model Assessment for Insulin Resistance

The homeostatic model assessment (HOMA) is a method used to quantify insulin resistance and beta-cell function (Homeostasis model assessment: insulin resistance and beta-cell function from fasting plasma glucose and insulin concentrations in man. Diabetologia 28: 412-9.). The approximating equation for insulin resistance, in the early model, used a fasting plasma sample, and was derived by use of the insulin-glucose product, divided by a constant.

$$\text{HOMA-IR} = (\text{Glucose} \times \text{Insulin})/405; \text{HOMA-}\%B = (20 \times \text{Insulin})/(\text{Glucose} - 63)$$

Where IR is insulin resistance and % B is the β-cell function where Glucose is given in mg/dl and Insulin is given in μU/mL (both during fasting). Garcinol inhibited insulin resistance assessed by HOMA-Index with significance when compared with the diabetic group. Moreover, β-cell function was significantly improved by Garcinol like that observed with glimepiride. The results are presented in table 2 below:

TABLE 2

Effect of Garcinol on HOMA-Index, and β-cell function

|  | HOMA-INDEX | % BETA-CELL FUNCTION |
|---|---|---|
| Normal | 1.47 ± 0.137* | 68 ± 70.5*** |
| Diabetic | 2.08 ± 0.174 | 14.8 ± 0.799 |
| Garcinol | 1.55 ± 0.0827* | 31.4 ± 3.17** |
| Olmesartan | 1.7 ± 0.095 | 21.7 ± 1.98 |
| Glimepiride | 1.53 ± 0.144 | 35.6 ± 5.24** |

The values are the means ± S.E.M. from five animals in each group.
*p < 0.05; *p < 0.01; *p < 0.001 vs. diabetic group.

Hemodynamic Parameters:

Hemodynamic parameters were measured using tail cuff apparatus (Non-invasive measurement of Blood Pressure-Kent Scientific, USA). Garcinol was also observed to improve the systolic, diastolic and mean Blood Pressure. The beneficial effect produced by garcinol administration was found to be independent of its effect on blood pressure. The results are presented in table 3 below:

TABLE 3

Effect of Garcinol on Hemodynamic parameters

|  | Before treatment | After Garcinol administration |
|---|---|---|
| Diastolic | 127 | 112 |
| Systolic | 165 | 153 |
| Mean | 139 | 125 |

Measurement of Renal Function and Biochemical Parameters

Biochemical estimation for glucose, insulin, albumin and total proteins; glomerular proteins (viz β-2 microglobulin, serum cystatin c and serum creatinine) for the determination of GFR; inflammatory cytokines and growth factors like Tumor necrosis factor (TNF-α), Nitric Oxide (NO), Transforming growth factor (TGF-$β_1$) and Vascular endothelial growth factor (VEGF) and kidney specific molecular markers involving adiponectin and erythropoietin were made in plasma/serum. The results of the experiment are presented in Table 4 below.

Furthermore, plasma insulin (p<0.01) levels were significantly increased, similar to that of olmesartan but less than glimepiride treatment in the treated diabetic rats as compared with diabetic groups after 8 weeks (Table 4):

TABLE 4

Effect of Garcinol administration on various biochemical and renal parameters

| Name of Parameter | Normal | Diabetic | Garcinol (200 mg/kg) | Olmesartan (6 mg/kg) | Glimepiride (1 mg/kg) |
|---|---|---|---|---|---|
| Biochemical parameters |  |  |  |  |  |
| Plasma Insulin (ng/ml) | 17.83 ± 3.2*** | 3.265 ± 0.36 | 12.13 ± 1.17** | 12.74 ± 1.48** | 14.38 ± 1.29*** |
| Total Proteins (mg/ml) | 2.144 ± 0.076*** | 1.368 ± 0.17 | 2.05 ± 0.14*** | 2.123 ± 0.11*** | 1.956 ± 0.09** |
| Serum Albumin (ng/ml) | 1.26 ± 0.26* | 0.14 ± 0.015 | 1.242 ± 0.1324* | 0.74 ± 101 | 1.08 ± 37.5* |
| GFR |  |  |  |  |  |
| Serum Creatinine (mg/dl) | 1.211 ± 0.21*** | 3.58 ± 0.18 | 1.804 ± 0.36** | 2.063 ± 0.41* | 1.873 ± 0.56** |
| Serum CystatinC (ng/ml) | 0.2298 ± 0.026*** | 0.644 ± 0.033 | 0.4098 ± 0.028** | 0.4617 ± 0.048* | 0.2933 ± 0.033*** |
| Beta-2 microglobulin (µg/ml) | 0.4419 ± 0.048** | 1.362 ± 0.12 | 0.3488 ± 0.12*** | 0.6529 ± 0.21* | 1.42 ± 0.21 |
| Inflammatory Markers |  |  |  |  |  |
| TNF-α (pg/ml) | 0.0176 ± 0.00545** | 0.427 ± 0.2198 | 0.04059 ± 0.0092** | 0.05665 ± 0.013** | 0.08563 ± 0.0167* |
| TGF-β (pg/ml) | 3.361 ± 0.98*** | 11.3 ± 1.348 | 3.908 ± 0.82*** | 5.963 ± 0.896** | 8.316 ± 2.06 |
| Nitric Oxide (nmol/µl) | 0.20 ± 0.027** | 0.59 ± 0.095 | 0.32 ± 0.026 | 0.34 ± 0.097 | 0.33 ± 0.064 |
| VEGF (pg/ml) | 48.5 ± 3.05*** | 74.08 ± 5.34 | 57.21 ± 3.89** | 66.3 ± 1.14 | 61.29 ± 2.54 |
| Molecular Markers |  |  |  |  |  |
| Adiponectin (µg/ml) | 3.393 ± 0.21** | 0.4 ± 0.089 | 3.297 ± 0.56** | 0.93 ± 0.18 | 2.277 ± 0.86 |
| Erythropoietin (mIU/ml) | 0.6775 ± 0.026*** | 0.128 ± 0.064 | 0.3508 ± 0.029 | 0.2657 ± 0.047 | 0.5141 ± 0.13** |

Further, there was also a significant improvement in levels of serum serum albumin and the rate of increase of creatine, cystain C and B-2M also decreased.

Histopathology

Kidney sections were stained with periodic acid-Schiff's reagent and Masson's modified trichrome to assess glomerulosclerosis and collagenous tubulointerstitial matrix, respectively.

Glomerulosclerotic Index

In 4 μm kidney sections stained with periodic acid-Schiff's reagent, 150 glomeruli from each animal were examined. The extent of sclerosis in each glomerulus was subjectively graded on a scale of 0 to 4, with the following grades: grade 0 normal, grade 1 sclerotic area <25% (minimal), grade 2 sclerotic area 25-50% (moderate), grade 3 sclerotic area 50-75% (moderate to severe) and grade 4 sclerotic area 75-100% (severe). A glomerulosclerotic index was then calculated using the formula:

$$GSI = \sum_{i=0}^{4} Fi\,(i)$$

Where GSI is glomerulosclerotic index, Fi is the % of glomeruli in the rat with a given score (i).

Quantitation of Matrix Deposition

The accumulation of matrix within the tubulointerstitial was assessed on Masson's trichrome stained sections. Blue area on a trichrome-stained section was selected for its color range and the proportional area of tissue with this range of color was then semi-quantified as tubulointerstitial matrix index (TIMI).

Immunohistochemistry for Nephrin:

Immunohistochemistry was done as previously described according to a modified method using a Polyclonal (C-Terminus) Antibody which is identical to rat nephrin. These experiments were done using 4 micron frozen kidney sections, as previously reported. Paraffin-embedded tissues sections were deparaffinized in microwave oven for 3 minutes. The sections were rehydrated in graded series of xylene and alcohols. Endogenous peroxidase activity was blocked by 3% hydrogen peroxide in distilled water for 15 minutes. Antigen retrieval was achieved by steam heating in a solution of citrate buffer, pH 6.0 for 30 minutes. Sections were blocked with 10% normal goat serum for polyclonal antibodies. Sections were then incubated for one hour with primary antibody Polyclonal (C-Terminus) Antibody which is identical to rat nephrin. The sections were then incubated in avidin-biotin complex at 1:25 dilution for 30 min at room temperature and developed using diaminobenzidine (DAB) as chromogen. After washing, the sections were counterstained with hematoxylin and coverslipped. Negative controls were carried out by incubation in the absence of the primary antibody. The quantification of nephrin was done using point counting technique for each animal as described in established method. Davis B J, Johnston C I, Burrell, L M, Burns W C, Kubota E, Cao Z, Cooper M E, Allen T J. Renoprotective effects of vasopeptidase inhibition in an experimental model of diabetic nephropathy. Diabetologia. 2003; 46(7): 961-71.

Figure 4:
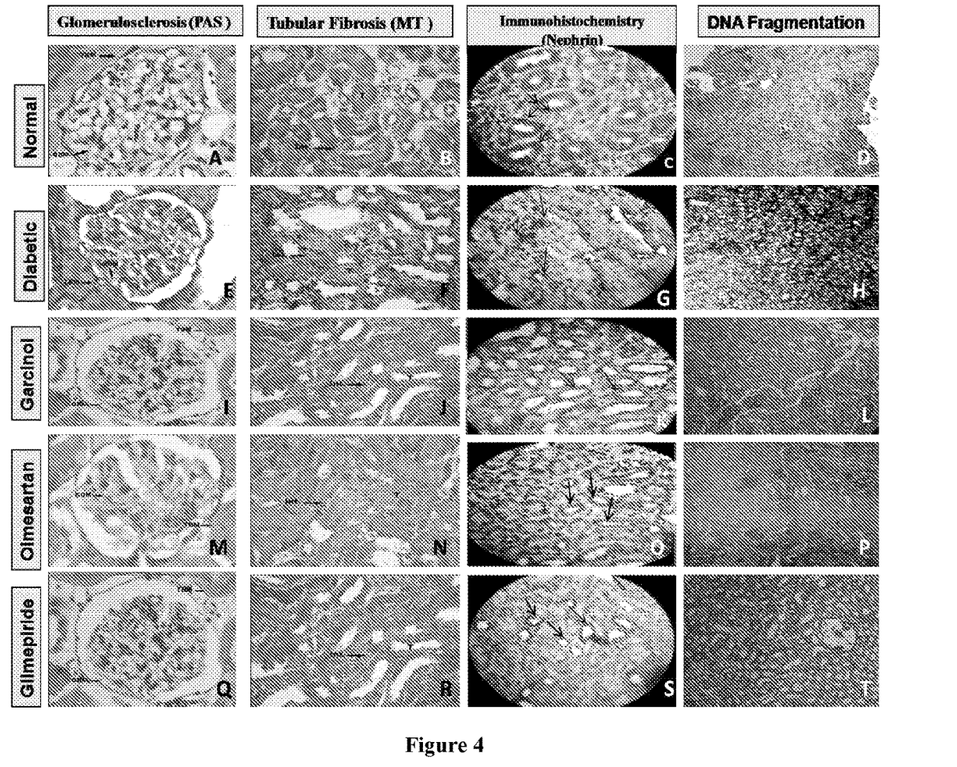
FIG. 4: illustrates the effect of 8 weeks dosing of Garcinol on histopathological changes and cellular apoptosis (using TUNNEL positive cells) in the kidney of STZ diabetic rats. Periodic acid-Schiff's reagent-stained, Masson's trichrome-stained, Nephrin expression and methylene green stained (for TUNNEL positive) sections are represented for (A, B, C, D) normal rats, (E, F, G, H) vehicle-treated diabetic rats, (I, J, K, L) Garcinol, (M, N, O, P) Olmesartan (6 mg/kg/day) and (Q, R, S, T) Glimepiride treated diabetic rats respectively. Original magnification×400. [GBM: Glomerular Basement Membrane; TBM: Tubular Basement Membrane; I: Interstitium; T: Tubule].

Histopathology study showed improved thickening of glomerular basement membrane in most glomeruli, reduced capillary occlusion, and mesangial expansion in diabetic rats treated with garcinol (FIG. 4). Consequently, the decrease in GSI observed in treatment with garcinol was comparable to olmesartan followed by glimepiride. Also, like glimepiride, in garcinol treated rats, collagen is visible in tubulo-interstitium of kidney cortex or medulla observed in diabetic control rats. Hence, TIMI was decreased with garcinol treatment when compared with the diabetic rats (Table 5):

TABLE 5 effects of Garcinol administration on Histopathological factors.

| Name of Parameter | Normal | Diabetic | Garcinol (200 mg/kg) | Olmesartan (6 mg/kg) | Glimepiride (1 mg/kg) |
|---|---|---|---|---|---|
| GSI |  |  | 1.4 | 1.4 | 2.8 |
| TIMI | 1 | 3 | 2 | 1 | 2 |
| Nephrin (% FA) | 70 | 3.7 | 50 | 62.5 | 20 |
| Apoptosis (% FA) | 2.5 | 87 | 20 | 40 | 90 |

However, the improvement in tubular injury was visible with olmesartan treatment (FIG. 4). In support to this, nephrin expression, qualitatively decreased in diabetic kidney, was observed to be improved by the garcinol treatment more than observed with either olmesartan or glimepiride (FIG. 4).

DNA Fragmentation Assay

For detection and localization of apoptosis in kidney, the technique of terminal deoxynucleotidyl transferase-mediated dUTP nick end labeling (TUNEL) (Apo-BrdU-IHC™ In Situ DNA Fragmentation Assay Kit, Biovison, USA) were employed. Briefly, sections were deparaffinized, hydrated, and digested with proteinase K (20 μg/ml), and then added biotinylated dUTP to the 3' end of DNA fragments by incubating sections in 0.05 mol/l Tris-HCl buffer (pH 7.6) with 0.03 U/μl TdT and 0.04 nmol/μl biotin-11-dUTP at 37° C. for 1 h. The sections were rinsed in PBS. Endogenous peroxidase was blocked with 0.3% $H_2O_2$ in distilled $H_2O$. The sections were rinsed with PBS and covers with 2% blocking solution in 0.1 mol/l sodium maleate to reduce background staining. The sections were then incubated with avidin-peroxidase complexes in PBS (1:50) for 30 min and rinsed with PBS (3×5 min). Peroxidase activity was visualized with 3,3'-diaminobenzidine until the brown product was clearly visible. The sections were then counterstained with methyl green. The positive apoptotic cells were the cells with brown nucleus 2.10.

Further, decrease in the DNA fragmentation was clearly observed qualitatively in the kidney of diabetic rats treated with garcinol and olmesartan. However, no change in the decrease in apoptosis was observed with the glimepiride treatment (FIG. 4).

Renal Function and Glomerular Filtration Rate

To assess renal function, albumin ($p<0.05$) and total proteins ($p<0.001$) levels were found to increase significantly in plasma/serum of garcinol treated diabetic rats from diabetic control rats (Table 2 above). The increased levels of total proteins and albumin was observed to be more than either of the reference standards used for the treatment. To further substantiate renal function, treatment with garcinol significantly reduced serum levels of creatinine ($p<0.01$), cystatin c ($p<0.01$) and beta 2 microglobulin ($p<0.001$) (Table2), thereby improving GFR. The GFR was observed to be significantly reduced than either of reference standards used. The area under the ROC curve for cystatin c was observed as 1.00 and that of creatinine was 0.8, indicating better diagnostic efficiency values for cystatin c than creatinine.

Inflammatory Markers and Growth Factors

The effect of garcinol on inflammation was evident from the decrease in TNF-alpha levels in plasma when compared with plasma levels of diabetic rat (P<0.05; Table 2), although the decrease was not more than observed with either olmesartan or glimepiride treatment. This was supported by decrease in nitric oxide levels more than either of reference treatments when compared with diabetic group (Table 2). Moreso, the plasma concentrations of TGF-β1 and VEGF in garcinol treated rats were decreased significantly (P<0.001) than the reference used in comparison with the diabetic group after 8-weeks (Table 2). In addition, kidney specific molecular markers viz. adiponectin and erythropoietin were found to increase with garcinol treatment, more than the reference used during the experiment in the treatment of diabetic rats.

In conclusion, present invention revealed that garcinol is effective in improving glucose homeostasis and metabolic profile in STZ rat model of diabetic mellitus with the defects in insulin sensitivity and secretion. The beneficial effect of garcinol on renal disorders, e.g., diabetic nephropathy is clearly associated with significant increase in nephrin, thickening of glomerular basement membrane and improve glomerular filtration rate.

Although the invention has been described with reference to specific embodiments, this description is not meant to be construed in a limiting sense. Various modifications of the disclosed embodiments, as well as alternate embodiments of the invention, will become apparent to persons skilled in the art upon reference to the description of the invention. It is therefore contemplated that such modifications can be made without departing from the spirit or scope of the present invention as defined.

We claim:

1. A method of providing Garcinol to a subject that has diabetic nephropathy comprising:
    selecting a subject that has diabetic nephropathy; and
    providing said subject an amount of Garcinol in the range of 100 mg/kg to 1000 mg/kg bodyweight of said subject, thereby inhibiting progression of diabetic nephropathy in the subject.

2. The method as claimed in claim 1, wherein the amount of Garcinol provided to said subject is about 200 mg/kg/day.

3. The method as claimed in claim 1, wherein Garcinol is provided orally or by injection.

4. The method as claimed in claim 1, wherein the rate of increase of serum creatinine is lowered in said subject.

5. The method as claimed in claim 1, wherein albuminuria is stabilized in said subject.

6. The method as claimed in claim 1, wherein the plasma protein levels, erythopoeitin levels, and/or adiponectin levels is increased in said subject.

7. The method as claimed in claim 1, wherein the expression of nephrin is increased in said subject.

8. The method as claimed in claim 1, wherein the rate of increase of cystatin c is increased in said subject, and the amount of B2M is decreased in said subject.

9. The method as claimed in claim 1, wherein glomerulosclerosis is reduced in said subject.

10. The method as claimed in 1, wherein the amount of nitric oxide is reduced in said subject.

11. The method as claimed in claim 1, wherein apoptosis is reduced in said subject.

12. The method as claimed in claim 1, wherein the expression of desmin is decreased in said subject.

* * * * *